(12) United States Patent
Massengale et al.

(10) Patent No.: US 7,470,266 B2
(45) Date of Patent: Dec. 30, 2008

(54) FLUID MEDICATION DELIVERY DEVICE

(75) Inventors: Roger Massengale, Mission Viejo, CA (US); Kevin M. Forrest, Rancho Santa Margarita, CA (US); Bill Porter, Carlsbad, CA (US); Donald M. Earhart, Irvine, CA (US); Alan Dine, Pleasant Plain, OH (US)

(73) Assignee: I-Flow Corporation, Lake Forest, CA (US)

( * ) Notice: Subject to any disclaimer, the term of this patent is extended or adjusted under 35 U.S.C. 154(b) by 586 days.

(21) Appl. No.: 10/663,362

(22) Filed: Sep. 16, 2003

(65) Prior Publication Data

US 2005/0058711 A1   Mar. 17, 2005

(51) Int. Cl.
*A61K 9/22* (2006.01)
(52) U.S. Cl. .................................. 604/890.1
(58) Field of Classification Search ............. 604/892.1, 604/67, 244, 891.1, 890.1; 424/448, 473, 424/449
See application file for complete search history.

(56) References Cited

U.S. PATENT DOCUMENTS

| | | | |
|---|---|---|---|
| 4,573,996 A | 3/1986 | Kwiatek et al. | |
| 4,605,399 A * | 8/1986 | Weston et al. | ............... 604/305 |
| 4,953,565 A | 9/1990 | Tachibana et al. | |
| 5,071,656 A | 12/1991 | Lee et al. | |
| 5,122,127 A | 6/1992 | Stanley | |
| 5,141,750 A | 8/1992 | Lee et al. | |
| 5,284,660 A | 2/1994 | Lee et al. | |
| 5,474,527 A | 12/1995 | Bettinger | |
| 5,770,220 A * | 6/1998 | Meconi et al. | ............... 424/448 |
| 5,785,688 A | 7/1998 | Joshi et al. | |
| 5,827,530 A * | 10/1998 | Reed, Jr. | ..................... 424/449 |
| 5,882,677 A | 3/1999 | Kupperblatt | |
| 6,068,853 A | 5/2000 | Giannos et al. | |
| 6,247,485 B1 | 6/2001 | Rossi et al. | |
| 6,350,253 B1 * | 2/2002 | Deniega et al. | ........ 604/164.02 |
| 6,375,978 B1 | 4/2002 | Kleiner et al. | |
| 7,004,923 B2 | 2/2006 | Deniega et al. | |
| 2003/0171710 A1 | 9/2003 | Bassuk et al. | |

* cited by examiner

*Primary Examiner*—Nicholas D Lucchesi
*Assistant Examiner*—Christopher D Koharski
(74) *Attorney, Agent, or Firm*—Knobbe Martens Olson & Bear LLP (57) ABSTRACT

A fluid delivery device is provided for transdermal delivery of fluid medications to patients. The device comprises a thin envelope which is applied to a patient's skin. The envelope comprises at least one diffusion layer coupled to at least one impermeable layer such that at least one chamber exists therebetween. Other embodiments include internal diffusion layers, and thus possess additional chambers, as well. The impermeable layer comprises a top surface of the device. A valve positioned in the impermeable layer facilitates filling the device with fluid, as well as connection of the device to external fluid sources such as an intravenous bag, pump, or other external fluid delivery system. The diffusion layer may comprise a semi-permeable membrane which controls the rate of fluid flow from the device to the patient's skin.

11 Claims, 10 Drawing Sheets

FLUID DIFFUSION
DIRECTION

FLUID DIFFUSION
DIRECTION

FLUID MEDICATION DELIVERY DEVICE

BACKGROUND OF THE INVENTION

1. Field of the Invention

This invention relates generally to fluid delivery devices, and relates more particularly to a fluid medication delivery device for application of fluid medications to a surface area of the skin of a patient.

2. Description of the Related Art

Transdermal patches are a known means for delivering pharmaceutical substances, such as fluid medications, to a patient by passing such fluids through the patient's skin. Transdermal patches are utilized for treatments such as hormone replacement therapy and smoking cessation. One type of transdermal patch contains an unreplenishable supply of a pharmaceutical substance. The patch has a skin-contacting adhesive layer to facilitate in adhering the patch to the skin. Typically, such a transdermal patch is adhered to a suitable area of the skin for a period of time, during which the substance is passed to the patient.

Once the pharmaceutical substance within the patch is substantially exhausted, the patch is removed from the skin. If more of the substance must be delivered to the patient, a subsequent patch must be applied and, in order to avoid irritation to the skin of the patient, often to a different location on the patient's skin. One drawback to using this type of transdermal patch is that a new area of the skin must be sought for the application of each subsequent patch. Thus, if such patches must be used for an extended period of time, it may become increasingly difficult to find an available area of the skin suitable for application of the patch. This difficulty becomes compounded if the skin-contacting adhesive of the patch is found to irritate the patient's skin. Another drawback is that such a transdermal patch contains a fixed initial quantity (i.e., volume) of a pharmaceutical substance, and thus individual patches are incapable of delivering large volumes of such substances, such as medicinal fluids.

Another type of patch includes an injection port that permits refilling of the patch with a pharmaceutical substance using a hypodermic needle. Although such an arrangement permits reuse of the patch, the refilling process should be carried out by a health care worker in order to prevent injury to the patient or damage to the patch due to the use of the hypodermic needle. As a result, frequent visits to a health care facility, or frequent home visits of a health care worker, are necessary to refill the patch. Accordingly, the convenience of such an arrangement is less than ideal. Furthermore, the use of a hypodermic needle presents a significant risk to the health care worker, as accidental pricking, or stabbing of the health care worker often accompanies to use of a hypodermic needle, or other sharp medical instrument.

Other patch-type fluid delivery arrangements allow for connection to an external fluid supply, but utilize complicated mechanisms for urging delivery of the pharmaceutical substance and/or do not provide for uniform delivery over the area of the patch. Accordingly, a need exists for an improved transdermal patch that overcomes the limitations of the prior art.

SUMMARY OF THE INVENTION

Preferred embodiments of the present fluid delivery device provide for transdermal delivery of fluid medications to a patient. In one arrangement, the device comprises a thin envelope, or pouch, which is attachable to a patient's skin. The envelope comprises at least one fluid semi-permeable layer coupled to at least one fluid impermeable layer such that at least one chamber, or fluid reservoir, exists within the envelope.

In other arrangements, at least one additional layer may be present. Preferably, the additional layer comprises a fluid impermeable layer with a plurality of openings therethrough. In one such arrangement, the impermeable layer comprises a top surface of the device. A one-way valve positioned in the impermeable layer facilitates filling the device with a fluid, as well as connecting the device to an external fluid source, such as an intravenous bag, pump, reservoir, or other external fluid delivery system.

In one arrangement, the fluid delivery device is filled with a volume of fluid and attached to the patient's skin, and thus functions as a portable source of fluid. In another arrangement, the fluid delivery device remains connected to an external fluid source. In such an arrangement, the device is capable of delivering a large volume of the fluid to the patient at a controlled flow rate over an extended period of time. In addition, such an arrangement facilitates temporary disconnection of the external fluid source without interruption of the delivery of fluid to the patient. Preferably, diffusion of the fluid through the device occurs under pressure imparted to the fluid by stretching of the impermeable layer(s) when the device is filled with the fluid and/or pressure supplied to the device by an external fluid source.

One aspect of the present invention involves a fluid medication delivery device including a fluid impermeable layer and a fluid semi-permeable layer. The semi-permeable layer and the impermeable layer cooperate to define a space therebetween. The space defines a fluid reservoir of the delivery device. The semi-permeable layer and the impermeable layer have a continuous seal therebetween to define a periphery of the fluid reservoir. A fluid inlet communicates with the fluid reservoir and comprises a valve configured to permit fluid entry into the fluid reservoir. In one arrangement, the valve is a one-way type valve that prevents the exiting of fluid from the reservoir through the inlet. The fluid inlet is adapted to permit connection to a supply of fluid. A fluid is diffusable across the semi-permeable layer, desirably, in response to either one of a pressure imparted on the fluid by the layers of the delivery device or a pressure imparted by an external source of fluid.

A further aspect of the present invention involves a fluid medication delivery device including a fluid impermeable pouch having first and second opposing walls. The first wall and the second wall define a space therebetween. The space defines a fluid reservoir of the delivery device. The second wall includes a plurality of openings therethrough defining a diffusion area of the delivery device. A fluid inlet communicates with the fluid reservoir and comprises a valve configured to permit fluid entry into the fluid reservoir. The fluid inlet is adapted to permit connection to a supply of fluid. A fluid semi-permeable layer covers at least the diffusion area of the delivery device and is configured such that fluid within the fluid reservoir must pass through the semi-permeable layer before exiting the delivery device.

Yet another aspect of the present invention involves a system for delivering a medicinal fluid to a dermal area of a patient. The system includes a delivery device having a fluid impermeable layer and a fluid semi-permeable layer cooperating to define a space therebetween. The space defines a fluid reservoir of the delivery device. A fluid inlet communicates with the fluid reservoir. A pump is configured to apply a pressure to a medicinal fluid and is connectable to the fluid inlet to supply a flow of the medicinal fluid to the fluid reservoir throughout a delivery cycle. When the infusion pump is connected to the fluid inlet, the medicinal fluid within the reservoir diffuses across the semi-permeable layer in response to the pressure applied by the infusion pump.

Still another aspect of the present invention involves a fluid medication delivery device including a fluid impermeable pouch having first and second opposing walls. The first wall and the second wall define a space therebetween. The space defines a fluid reservoir of the delivery device. The second wall includes a plurality of openings therethrough defining a diffusion area of the delivery device. A coiled wire member covers at least the diffusion area of the delivery device and is constructed of a plurality of adjacent wire sections defining a plurality of gaps therebetween. The coiled wire member is configured such that fluid within the fluid reservoir must pass through the coiled wire member before exiting the delivery device.

BRIEF DESCRIPTION OF THE DRAWINGS

These and other features, aspects and advantages of the present invention are described with reference to drawings of several preferred embodiments, which are intended to illustrate, but not to limit, the present invention. The drawings include twenty-two figures.

DETAILED DESCRIPTION OF THE PREFERRED EMBODIMENTS

Although certain preferred embodiments and examples are disclosed below, it will be understood by those skilled in the art that the invention extends beyond the specifically disclosed embodiments to alternative embodiments and/or uses of the invention and obvious modifications and equivalents thereof. Thus, it is intended that the scope of the invention herein disclosed should not be limited by the particular embodiments described below.

FIGS. 1 through 4 illustrate a preferred embodiment of a fluid delivery device, generally referred to by the reference numeral 10. The fluid delivery device 10 includes a thin, circular pouch, or envelope 12, which is adapted for placement on the skin of a patient. Preferably, an inlet valve assembly 14 permits fluid communication with an interior space of the envelope 12.

As illustrated in FIGS. 1 through 4, preferably, the envelope 12 is constructed of a fluid impermeable sheet 18, and a fluid semi-permeable sheet, or diffusion sheet 20, which permits fluid to pass therethrough at a substantially uniform rate. In the illustrated embodiment, outer edge portions of the impermeable sheet 18 and the diffusion sheet 20 are secured to one another by a peripheral seal 16, such that a substantially fluid tight interior chamber 22 is formed therebetween. Thus, the peripheral seal 16 defines a periphery of the interior chamber 22, or a fluid reservoir of the delivery device 10. The seal 16 may be constructed in any suitable manner. For example, the seal 16 may be created by heat bonding, chemical bonding, or RF welding, for example, but without limitation. In addition, one or more additional components may be utilized to form the seal 16, such as an overlapping or reinforcing member, for example. Other methods of creating a substantially fluid tight interior chamber apparent to one of skill in the art may also be used.

An outwardly facing surface of the impermeable sheet 18 defines a top surface of the device 10, which preferably does not contact the patient's skin. An outwardly facing surface of the diffusion sheet 20 defines a bottom, contact surface of the device 10, which is placed on the patient's skin during operation of the device 10. In such an arrangement, adhesive, preferably in the form of an adhesive layer, may be present on the exposed portion of a lower surface of the diffusion sheet 20 to assist in securing the device 10 to the skin of the patient. The adhesive may be provided on the entire external surface of the diffusion sheet 20 or on only a portion of the external surface, such as a peripheral portion, for example. Although not specifically illustrated, an addition, removable protective sheet may be provided to protect the adhesive, and maintain sterility, before use of the device 10. In addition, such a layer may prevent fluid from exiting the reservoir through the diffusion sheet 20, when attached to the device 10, to permit the device 10 to be prefilled with a fluid.

In alternative arrangements, the impermeable sheet 18 and the diffusion sheet 20 may not necessarily be of the same size and shape. In one such arrangement, the upper, impermeable sheet 18, may be larger than the lower, diffusion sheet 20 and, thus, a portion of the impermeable sheet 18 may contact the skin of the patient. Alternatively, other suitable means for securing the device 10 to the skin of the patient may be utilized, such as another layer, an external wrapping, for example, alone or in combination with adhesive provided on the device 10, as is described in greater detail below with reference to FIGS. 5 and 6.

Preferably, the diffusion sheet 20 is at least partially constructed from a biocompatible material suitable for exposure to the types of medicinal fluids contemplated, as will be readily appreciated by one of skill in the art. In the embodiment illustrated in FIGS. 1 through 4, the diffusion sheet 20 is constructed from a semi-permeable membrane configured to control the rate of fluid flow therethrough, as well as provide for uniform distribution of the fluid.

The semi-permeable membrane, or porous membrane, includes a plurality of pores, or tortuous passages extending therethrough. Preferably, each of the pores have a diameter of no more than about 0.25 μm. As will be appreciated by one of skill in the art, it is not necessary that the pores be circular in cross-sectional shape. Accordingly, the recitation of the pores having a diameter is not intended to be a limitation on the present invention. Rather, it is assumed that the cross-sectional shape can be assumed to be circular for the purpose of describing passages of such a size.

Suitable materials from which the semi-permeable membrane may be constructed include, without limitation, polyethylene, polysulfone, polyethersulfone, polyvinylidene, diflouride, polycarbonate, nylon, high density polyethylene, polytetrafluoroethylene, or other similar materials. Other materials that may comprise the diffusion sheet 20 include, but are not limited to, suture materials, surface coated and/or treated metals such as stainless steel, and ferrous/nonferrous alloys. In other embodiments, however, the diffusion sheet 20 may be supplemented or replaced by a perforated impermeable sheet, coiled spring, coiled wire/cord, or another similar device for controlling the rate and distribution of fluid flowing from the interior chamber 22 to the patient's skin, as is described in greater detail below.

Figure 1:
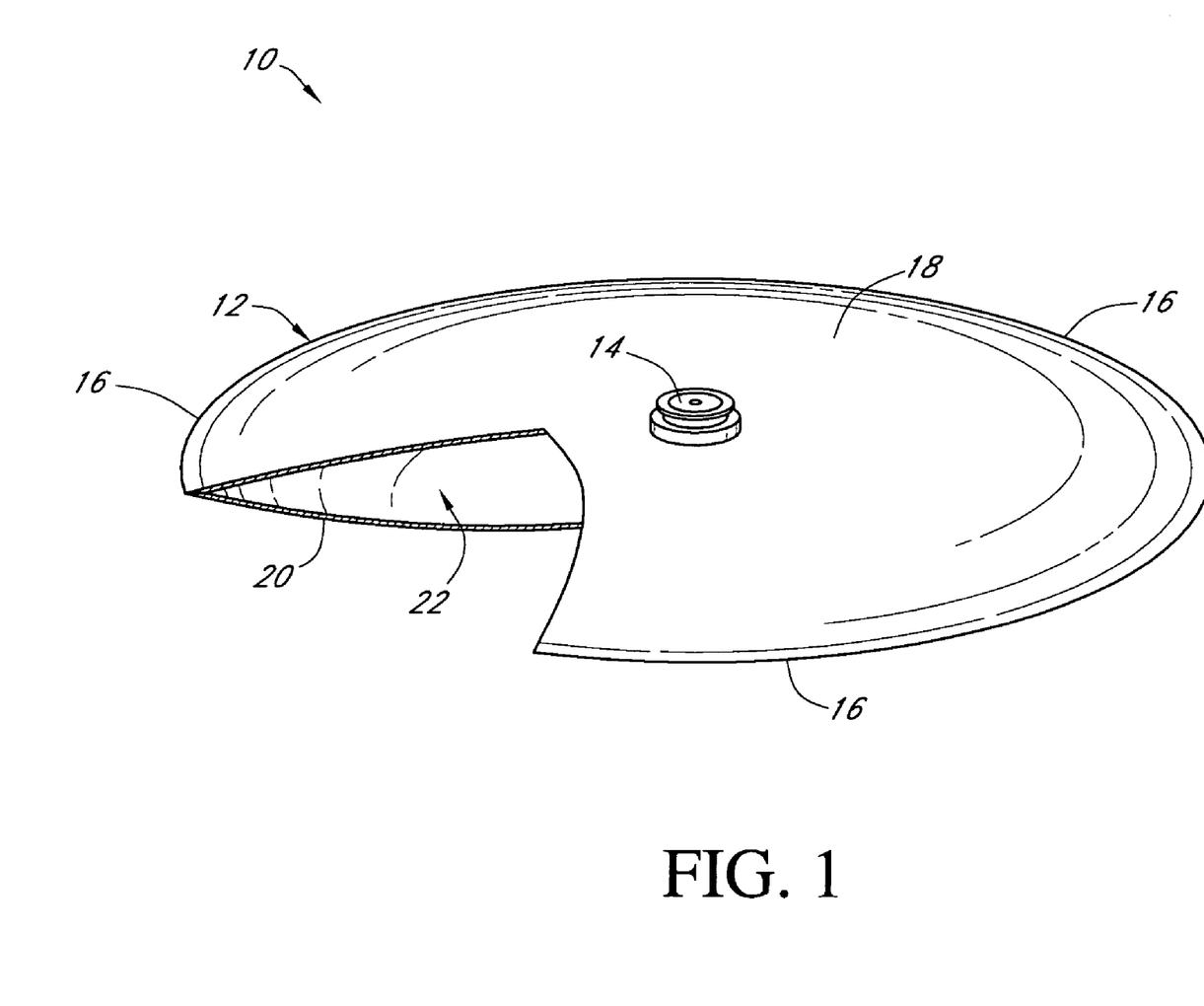
FIG. 1 is a perspective, partial cutaway view of a fluid delivery device. The fluid delivery device of FIG. 1 includes a fluid impermeable layer and a fluid semi-permeable layer joined by a circumferential seal and defining a fluid reservoir therebetween. A fluid inlet permits entry of fluid into the fluid reservoir.
Figure 2:
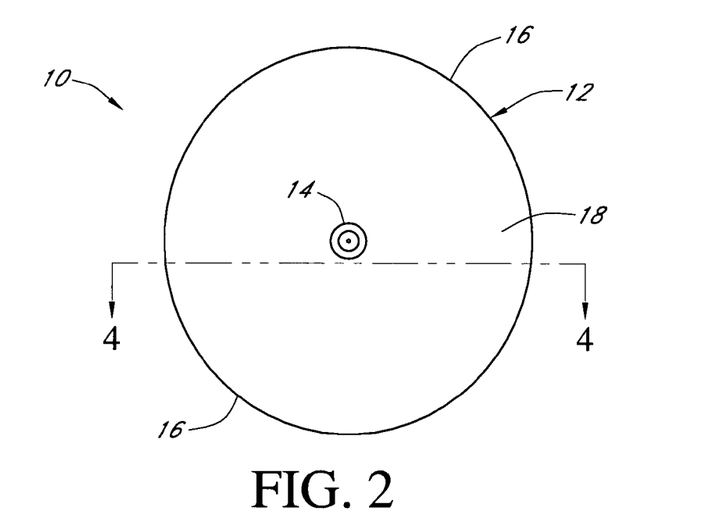
FIG. 2 is a top view of the fluid delivery device of FIG. 1.
Figure 3:
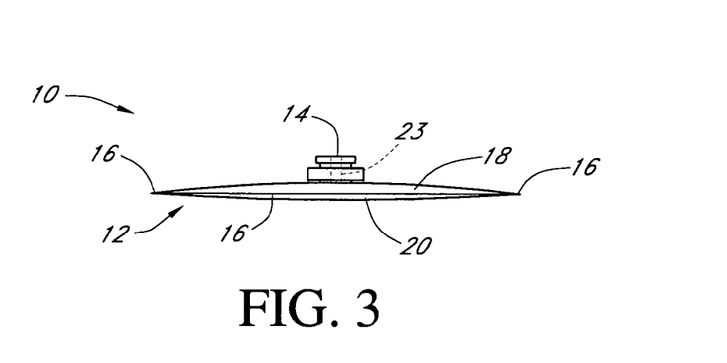
FIG. 3 is a side elevation view of the fluid delivery device of FIG. 1.
Figure 4:
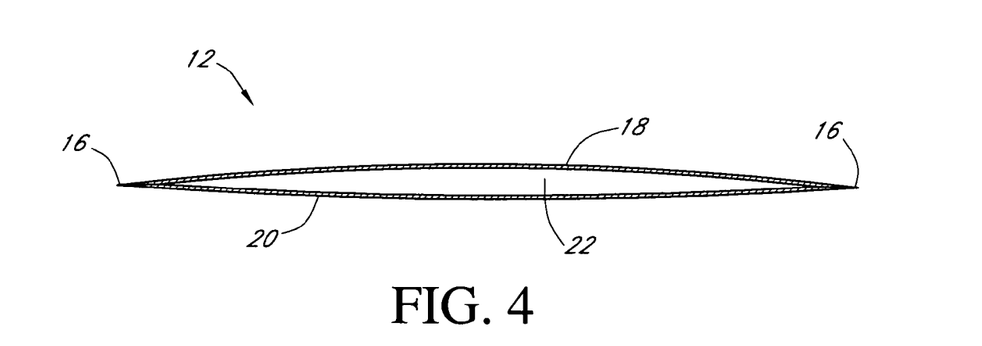
FIG. 4 is a cross-sectional view of the fluid delivery device of FIG. 1, taken along line 4-4 of FIG. 2.

As illustrated in FIGS. 1 through 3, preferably the valve 14 is centrally positioned on the impermeable sheet 18. In other embodiments, the valve 14 may be positioned in other locations on the impermeable sheet 18 or other locations of the device 10 that permit communication with the interior chamber 22. The illustrated valve 14 defines an inlet passage 23 (FIG. 3) that permits fluid communication from the outside environment to the interior chamber 22. Preferably, the valve 14 is a "one-way" valve assembly. That is, the valve 14 allows fluid communication from the outside environment to the interior chamber 22, while substantially preventing fluid within the interior chamber 22 from exiting through the valve 14. Any suitable construction may be used to provide the "one-way" function of the valve 14, as will be appreciated by one of skill in the art.

Desirably, the valve 14 is adapted to receive a coupler, such as a luer connector, to permit the coupling of an external fluid supply source, or pressure source, to the device 10. In addition, other suitable types of connection assemblies may also be used. Advantageously, the "one-way" nature of the valve 14 permits coupling, and uncoupling, of an external device to the delivery device 10 without loss of fluid from the interior chamber 22. Furthermore, a cap (not shown) may be provided to cover and protect the valve 14 from damage or contamination.

The illustrated fluid delivery device 10 is particularly well-suited for the continuous delivery of fluid medication(s), such as antibiotics, local anesthetics, drug "cocktails", and/or other fluid substances, to a surface area of the skin of a patient. The surface area may be of a wide variety of shapes and sizes and may consist of wound sites, burns, skin grafts or other such treatment areas of the skin surface.

Figure 5:
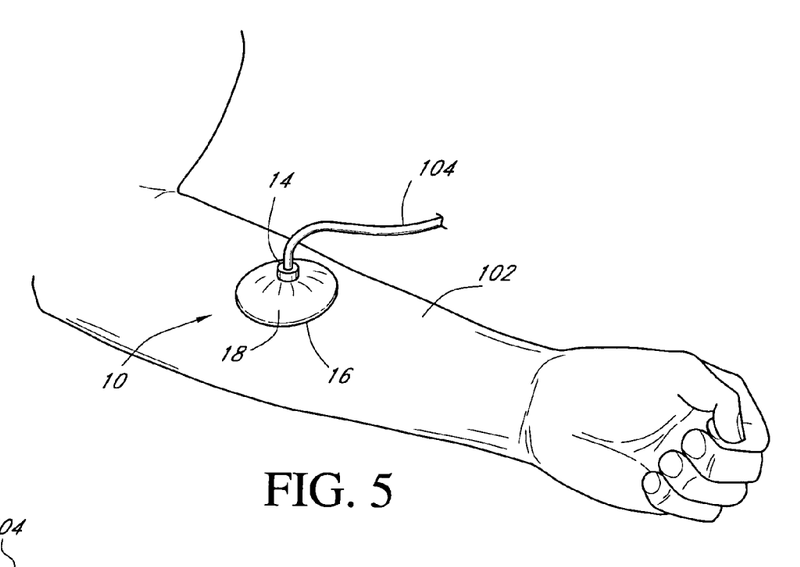
FIG. 5 is a perspective view of one exemplary environment of use of the fluid delivery device of FIG. 1, wherein the device is utilized to deliver fluid to the forearm of a patient.
Figure 6:
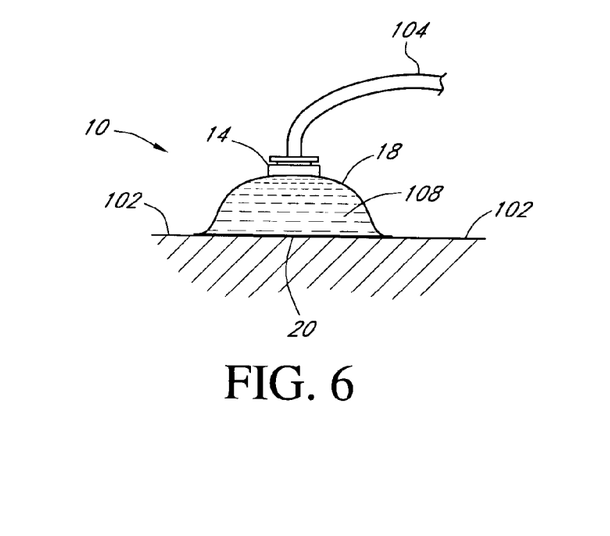
FIG. 6 is a cross-sectional view of the exemplary use environment of FIG. 5, illustrating a volume of fluid contained within the fluid reservoir of the delivery device.

FIGS. 5 and 6 illustrate one such exemplary use environment wherein the fluid delivery device 10 is utilized to deliver a fluid 108 to the skin of a forearm 102 of a patient. Although not shown in FIGS. 5 and 6, a sterile dressing, such as a bandage or elastic wrap, may be used to fix the device 10 in position on the forearm 102. The sterile dressing may also be used to apply a force to the device 10 in order to pressurize the fluid 108 therein. The sterile dressing may be utilized to pressurize the fluid 108 in addition to pressure supplied by an external source of fluid (not shown) and/or the device 10 itself, or the sterile dressing may be the only means of pressurizing the fluid.

In the illustrated arrangement, a tube 104 is connected to the valve 14 of the fluid delivery device 10. It is contemplated that the valve 14 and the tube 104 place the device 10 in fluid communication with an external fluid source (not shown), such as an intravenous bag, pump, reservoir, or other external fluid delivery system. Once the fluid delivery device 10 is filled with a volume of the fluid 108, as shown in FIG. 6, the tube 104 may be disconnected from the valve 14. The one-way feature of the valve 14 ensures that the fluid does not leak from the interior chamber 22. With the tube 104 disconnected, the fluid delivery device 10 functions as a portable source of the fluid 108 to the patient. However, as will be appreciated by one of skill in the art, the valve 14 may also be a two-way valve, which permits fluid 108 to both enter and exit the reservoir through the valve 14.

In such an arrangement, when the interior chamber 22 of the device 10 is filled with the fluid 108, pressure is imparted to the fluid 108 preferably by stretching of the impermeable sheet 18 of the device 10. This pressure causes the fluid 108 to diffuse from the interior chamber 22 to the forearm 102. However, it is not necessary that the upper and lower sheets 18, 20 be capable of stretching. The fluid 108 may nonetheless diffuse through the diffusion sheet 20 without pressure imparted by the impermeable sheet 18 or diffusion sheet 20. Desirably, the diffusion sheet 20 influences the flow rate of the fluid 108 and uniformly distributes the fluid 108 on the skin. Specifically, in a preferred arrangement, the pore size of the diffusion sheet 20 determines the flow rate of the fluid 108 from the device 10.

In an alternative arrangement, the tube 104 (and the external fluid source) may remain connected to the one-way valve 14 so that the device 10 continuously delivers the fluid 108 to the patient at a controlled flow rate. With this method, preferably diffusion of the fluid 108 through the device 10 occurs under a combination of pressure imparted to the fluid 108 by the internal system pressure of the delivery device 10, as discussed above, and pressure supplied by the external fluid source. The delivery of fluid 108 may continue until the external supply of fluid is exhausted. In other words, the external fluid supply determines the duration of the delivery cycle. In fact, due to the internal reservoir (e.g., the interior chamber 22) of the delivery device 10, the external fluid supply may be replaced once empty while delivery of the fluid 108 continues as a result of the internal system pressure of the device 10 and the fluid 108 remaining within the reservoir 22. Thus, the external fluid supply may be replenished, without interrupting delivery of fluid 108 to the patient.

In use, preferably, the protective sheet, if provided, is removed from the device 10 and the device 10 is applied to a desired area of the skin of the patient, such as the forearm 102, for example. The device 10 is connected to the external source of fluid by connecting the tube 104 to the valve 14 of the fluid delivery device 10. The reservoir 22 of the device 108 is filled with fluid 108 from the external fluid source. Once the reservoir 22 is filled to a sufficient level, fluid begins to diffuse across the diffusion sheet 20 and through the skin of the patient. If desired, an external wrapping, such as a sterile bandage or dressing, may be applied over the fluid delivery device 10 to protect the device 10, maintain sterile conditions, and/or assist in diffusion of the fluid 108.

When the external source of fluid has been substantially depleted, the tube 104 may be disconnected from the device 10 and the external wrapping (if any) and device 10 may be removed from the patient. Alternatively, the tube 104 may be disconnected from the device 10 and another external fluid source may be connected to the device 10. Thus, the external fluid source may be renewed without removing the device 10 from the patient. Furthermore, if fluid 108 is still present within the reservoir 22 when the external fluid source is disconnected, a replenished fluid source may be connected to the device 10 and begin delivering fluid to the delivery device 10. Thus, fluid delivery to the patient may proceed uninterrupted during replenishment of the external fluid source.

Figure 7:
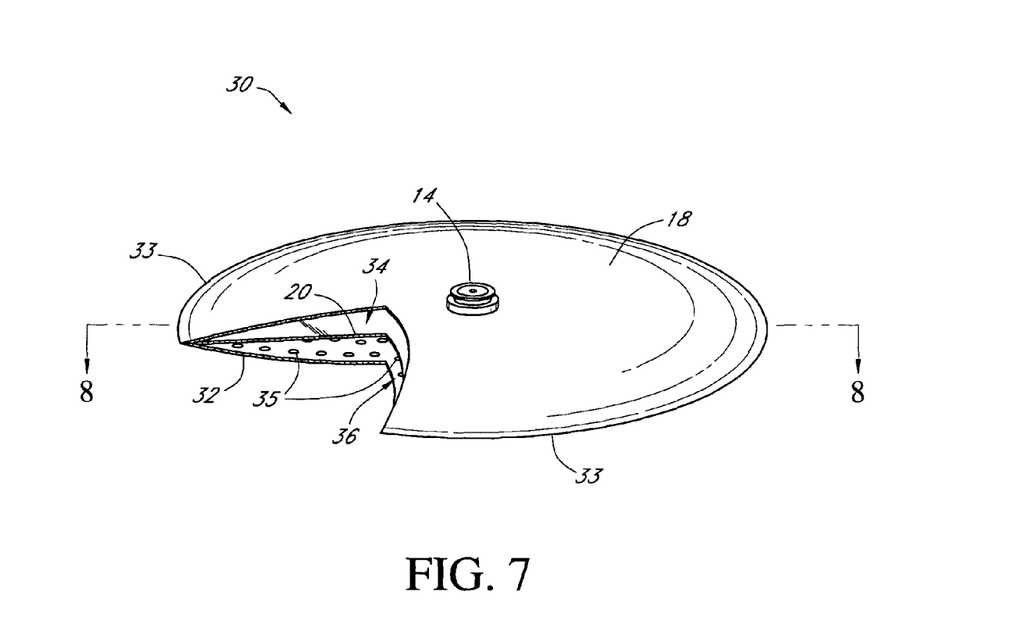
FIG. 7 is a perspective, partial cutaway view of another embodiment of a fluid delivery device. The device of FIG. 7 includes upper and lower fluid impermeable layers. The lower impermeable layer includes a plurality of openings configured to allow fluid to pass therethrough. A fluid semi-permeable layer is positioned between the upper and lower layers and is configured to cover the plurality of openings.
Figure 8:
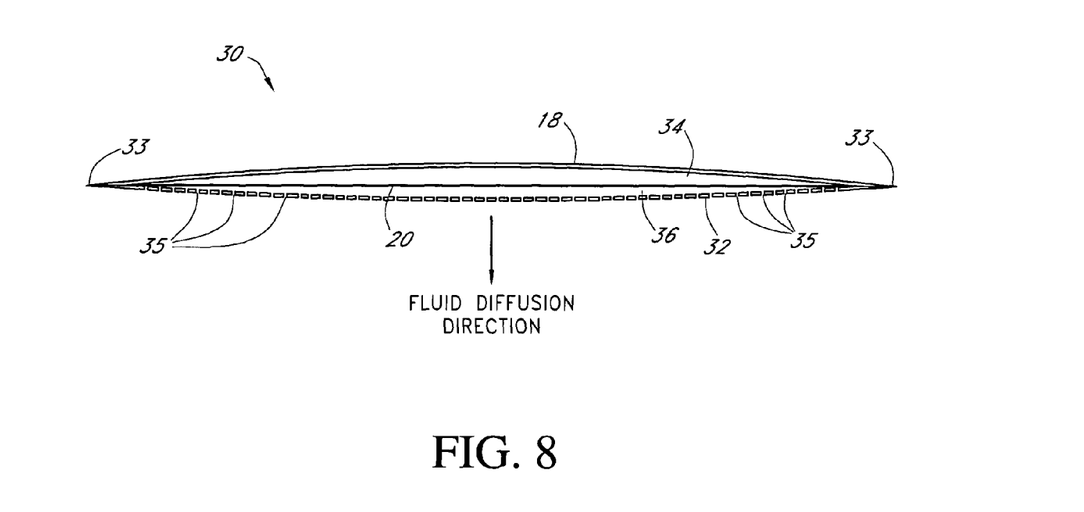
FIG. 8 is a cross-sectional view of the fluid delivery device illustrated in FIG. 7, taken along line 8-8 of FIG. 7.

FIGS. 7 and 8 illustrate a modification of the delivery device 10 of FIGS. 1-6, and is generally referred to by the reference numeral 30. Like components are designated with like reference numerals throughout the figures. The delivery device 30 is also adapted for placement on the skin of a patient and, preferably, is substantially similar to the fluid delivery device 10. However, the delivery device 30 of FIGS. 7 and 8 is comprised of more than two layers. Specifically, the device 30 includes an impermeable sheet 18, a fluid semi-permeable diffusion sheet 20 and a lower impermeable sheet 32. Similar to the device 10 described above, the sheets 18, 20, 32 are attached to one another by a peripheral seal 33 such that the diffusion sheet 20 defines a first chamber 34 and a second chamber 36 between the impermeable sheets 18, 32, respectively. The first and second chambers 34, 36, collectively, define a fluid reservoir of the device 30. In an alternative arrangement, the diffusion sheet 20 and the lower impermeable sheet 32 may be bonded together, thereby eliminating the second chamber 36. The sheets 20, 32 thus form a compound sheet that, preferably, controls the flow rate and distribution of fluid passing from the first chamber 34 to the skin of the patient.

In the illustrated embodiment, the diffusion sheet 20 is of a substantially similar size and shape as the upper and lower sheets 18, 32. However, in an alternative arrangement, the diffusion sheet 20 may be smaller than either of the upper and lower sheets 18, 32 and may be secured to the lower sheet 32 separately from the peripheral seal 33. For example, the diffusion sheet 20 may cover only a portion of the lower, impermeable sheet 32 and may be secured to the sheet 32 by a seal separate from, but similar to, the peripheral seal 33. In such an arrangement, preferably, openings in the lower sheet 32 are provided only within the area covered by the diffusion sheet 20. That is, desirably, the device 30 is arranged such that fluid within the reservoir 34 must pass through the diffusion sheet 20 before exiting the device 30 so that the flow rate of the fluid remains substantially uniform.

A valve 14 is positioned on the impermeable sheet 18 and facilitates fluid communication from the outside environment to the first chamber 34. The valve 14 preferably is a one-way valve, which is adapted to receive a coupler, such as a luer connector. The one-way valve 14 facilitates filling the first chamber 34 with a fluid and/or connecting the first chamber 34 to an external fluid source (where employed).

The lower impermeable sheet 32 defines at least a portion of a bottom surface of the device 30, which is placed in contact with the patient's skin during use of the device 30. As illustrated in FIG. 7, preferably the lower impermeable sheet 32 has a plurality of passages 35 that allow passage of the fluid from the second chamber 36 to the patient's skin. Preferably, the passages comprise small diameter, circular holes. Desirably, the holes 35 each have a diameter ranging between about 0.25 µm and about 0.254 mm. Furthermore, preferably, the holes 35 are distributed substantially evenly over the lower impermeable sheet 32, or a substantial portion thereof. The region of the lower impermeable sheet 32 that includes the holes 35 generally defines a diffusion section of the delivery device 30. That is, fluid within the device 30 is delivered in a substantially uniform manner over the diffusion section.

Preferably, use of the fluid delivery device 30 is substantially similar to the operation of the fluid delivery device 10 of FIGS. 1-6. However, fluid entering the device 30 via the valve 14 enters the first chamber 34 and then is diffused into the second chamber 36, through the diffusion sheet 20, before passing through the openings 35 of the lower impermeable sheet 32 to the patient's skin. In operation, the first chamber 34 is filled with a volume of fluid and the diffusion sheet 20 allows the fluid to pass from the first chamber 34 into the second chamber 36 at a controlled flow rate. The plurality of small holes 35 in the lower impermeable sheet 32 uniformly distributes the fluid as it passes from the second chamber 36 to the skin of the patient.

As discussed above with reference to FIGS. 5 and 6, it is contemplated that a tube may be connected to the valve 14 of the device 30, thereby placing the first chamber 34 in fluid communication with an external fluid source (not shown), such as an intravenous bag, pump, reservoir, or other external fluid delivery system. In one arrangement, the fluid delivery device 30 may be filled with a volume of fluid and then the tube disconnected from the valve 14. Upon disconnection of the tube, the fluid delivery device 30 functions as a portable source of the fluid to the patient. It will be appreciated that when the first chamber 34 of the device 30 is filled with the fluid, desirably, pressure is imparted to the fluid by stretching of the impermeable sheet 18 of the device 30 and/or by an external dressing, as described above. This pressure causes the fluid to diffuse from the first chamber 34 to the second chamber 36 at a controlled rate and then to flow to the patient's skin through the holes 35.

Alternatively, the tube (and the external fluid source) may remain connected to the valve 14 so that the device 30 continuously delivers the fluid to the patient at a controlled flow rate. Thus, preferably, diffusion of the fluid through the device 30 occurs under a combination of pressure imparted to the fluid by stretching of the impermeable sheet 18 and pressure supplied by the external fluid source.

Figure 9:
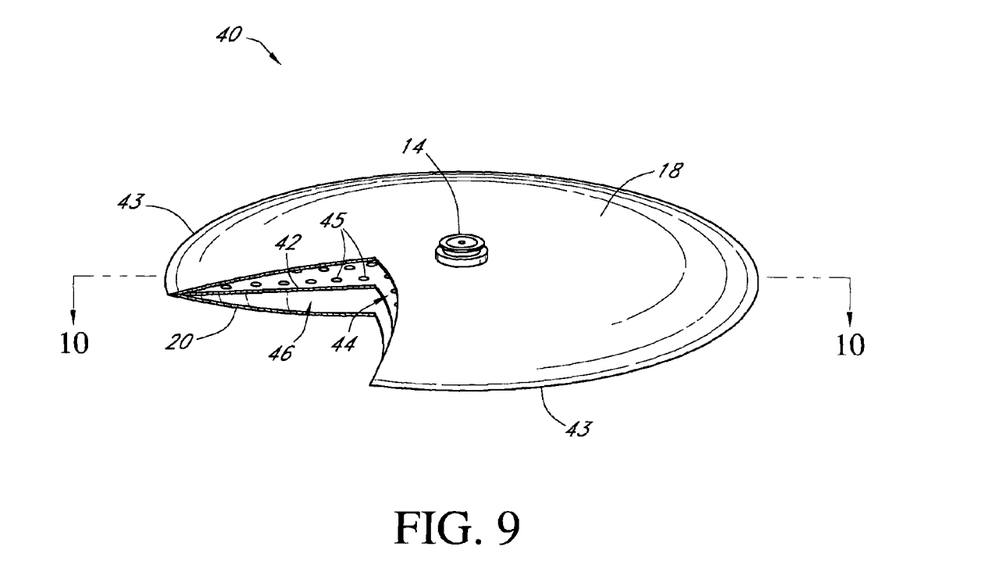
FIG. 9 is a perspective, partial cutaway view of yet another embodiment of a fluid delivery device. The device of FIG. 9 includes upper and lower fluid impermeable layers, with the lower layer including a plurality of openings configured to allow fluid to pass therethrough. A fluid semi-permeable layer is positioned adjacent an external surface of the lower layer and is configured to cover the plurality of openings.
Figure 10:
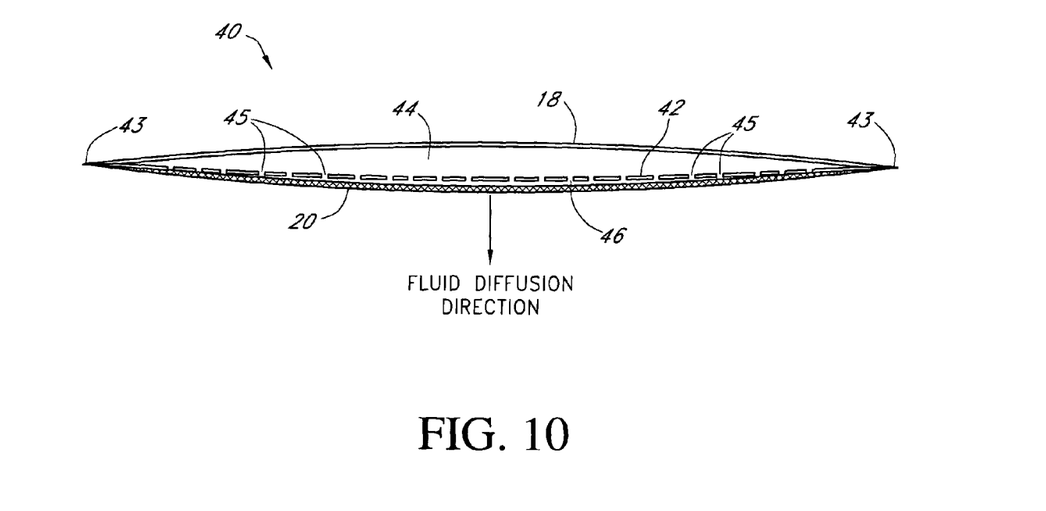
FIG. 10 is a cross-sectional view of the fluid delivery device illustrated in FIG. 9, taken along line 10-10 of FIG. 9.

FIGS. 9 and 10 illustrate another embodiment of a fluid delivery device 40, which is adapted for placement on the skin of a patient. The fluid delivery device 40 shown in FIGS. 9 and 10 is substantially similar to the fluid delivery device 10, illustrated in FIGS. 7 and 8, with the exception that the lower impermeable sheet 42 is positioned between the diffusion sheet 20 and the upper impermeable sheet 18. As in the previous embodiments, preferably, the impermeable sheets 18, 42 and the diffusion sheet 20 are attached to one another by a peripheral seal 43 such that the lower impermeable sheet 42 defines a first chamber 44 and a second chamber 46 between the impermeable sheet 18 and the diffusion sheet 20, respectively. The impermeable sheets 18, 42 may be made of plastic or other similar material, as described above.

Preferably, a valve 14 is positioned on the impermeable sheet 18 and provides fluid communication from the outside environment to the first chamber 44. The valve 14 is configured to allow fluid to enter the first chamber 44 without fluid leaking back to the outside environment. The valve 14 preferably is adapted to receive a coupler, such as a luer connector. The valve 14 facilitates filling the first chamber 44 with a fluid and/or connecting the first chamber 44 to an external fluid source (where employed).

As illustrated in FIG. 9, the lower impermeable sheet 42 (intermediate layer) includes a plurality of small diameter holes 45, which uniformly distribute fluid flow from the first chamber 44 to the second chamber 46. Desirably, each of the holes 45 has a diameter of between about 0.25 µm and about 0.254 mm. Fluid in the second chamber 46 then passes through the diffusion sheet 20 to the patient's skin. As discussed with reference to FIGS. 1-4, preferably, the diffusion sheet 20 is comprised of a semi-permeable membrane which controls the rate of flow to the skin, as well as uniformly distributing the fluid passing through the diffusion sheet 20. The diffusion sheet 20 comprises a bottom surface, which defines at least a portion of the skin contact surface of the device 40. In another embodiment, the sheets 20, 42 are bonded together, thereby eliminating the second chamber 46. In this embodiment, the sheets 20, 42 comprise a compound sheet that controls the flow rate and distribution of fluid passing from the first chamber 44 to the patient's skin.

It will be appreciated that the fluid delivery device 40 may be utilized for continuous delivery of fluid medication(s), such as antibiotics, local anesthetics, drug "cocktails", and/or other fluid substances, to a surface area such as a wound site or treatment area on a patient's skin. Operation of the fluid delivery device 40 is substantially similar to the operation of the fluid delivery device 30, described above. In operation, fluid entering the device 40 via the valve 14 enters the first chamber 44 and then is distributed into the second chamber 46 (where employed) before being controllably passed on to the patient's skin. When the device 40 is placed on the skin and the first chamber 44 is filled with a volume of fluid, the holes 45 in the lower impermeable sheet 42 uniformly the fluid from the first chamber 44 into the second chamber 46. The diffusion sheet 20 then allows the fluid to pass at a controlled flow rate from the second chamber 46 to the skin of the patient.

As discussed above with reference to FIGS. 5 and 6, it is contemplated that a tube may be connected to the valve 14 of the device 40, thereby placing first chamber 44 in fluid communication with an external fluid source (not shown), such as an intravenous bag, pump, reservoir, or other external fluid delivery system. In one embodiment, the fluid delivery device 40 may be filled with a volume of fluid and then the tube disconnected from the valve 14. The fluid delivery device 40 then functions as a portable source of the fluid to the patient. It will be appreciated that when the first chamber 44 of the device 40 is filled with the fluid, pressure is imparted to the fluid by stretching of the impermeable sheet 18 and/or by an external wrap, or dressing, as described above. This pressure causes the fluid to flow from the first chamber 44 to the second chamber 46 and then diffuses controllably to the patient's skin.

Alternatively, the tube (and the external fluid source) may remain connected to the valve 14 so that the device 40 continuously delivers the fluid to the patient at a controlled flow rate. With the tube connected to the valve 14, diffusion of the fluid through the device 40 desirably occurs under a combination of pressure imparted to the fluid by stretching of the impermeable sheet 18 and pressure supplied by the external fluid source.

It will be appreciated that depending on the particular surface area requiring treatment, the fluid delivery devices 10, 30 and 40 may advantageously be configured with a variety of shapes and sizes, as well as combinations thereof. FIGS. 11 through 15 illustrate several embodiments of fluid delivery devices having advantageous shapes and sizes. It is to be noted, however, that other shapes and sizes than those shown herein, as well as combinations of these and other shapes and sizes providing still more complex shapes, are contemplated and thus fall within the scope of the present invention.

Figure 11:
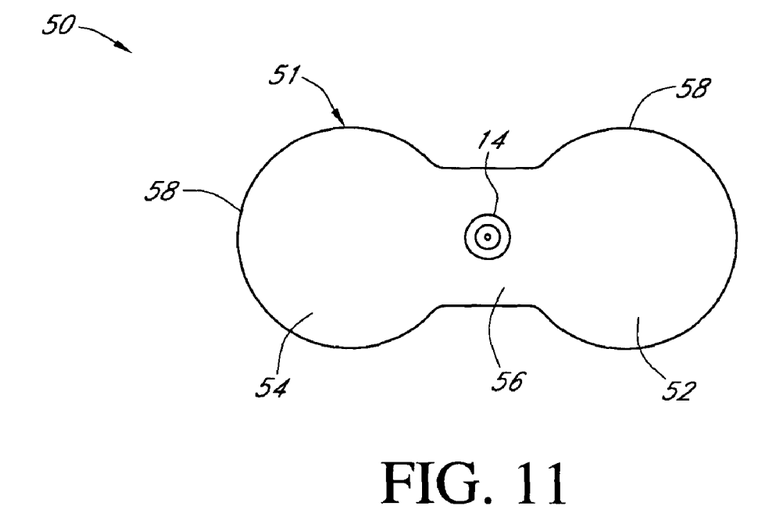
FIG. 11 is a top view of an embodiment of a fluid delivery device having a dog-bone outer shape.

FIG. 11 illustrates an embodiment of a fluid delivery device 50 comprising an envelope 51 and a valve 14. The envelope 51 comprises a first circular portion 52 and a second circular portion 54 interconnected by a rectangular bridge portion 56. The valve 14 is of the "one-way" variety and is adapted to receive a luer connector. It is contemplated that the device 50 may comprise any number and/or combination of the sheets and the interior chambers discussed above with reference to FIGS. 1 through 10. As with the devices 10, 30, 40, the sheets comprising the fluid delivery device 50 are attached to one another by a peripheral seal 58. Operation of the fluid delivery device 50 is substantially similar to the operation of the devices 10, 30 or 40.

Figure 12:
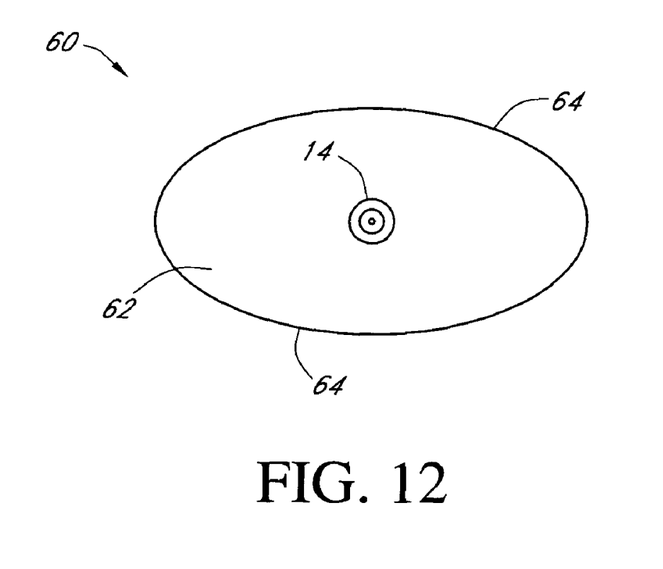
FIG. 12 is a top view of an embodiment of a fluid delivery device having an oval outer shape.

FIG. 12 illustrates an embodiment of a fluid delivery device 60 comprising an oval envelope 62 including a one-way valve 14. It is contemplated that the device 60 may comprise any number and/or combination of the sheets discussed herein, and are sealed to one another by a peripheral bond 64. Depending on the sheets utilized within the oval envelope 62, operation of the fluid delivery device 60 is substantially similar to the operation of the devices 10, 30 or 40.

Figure 13:
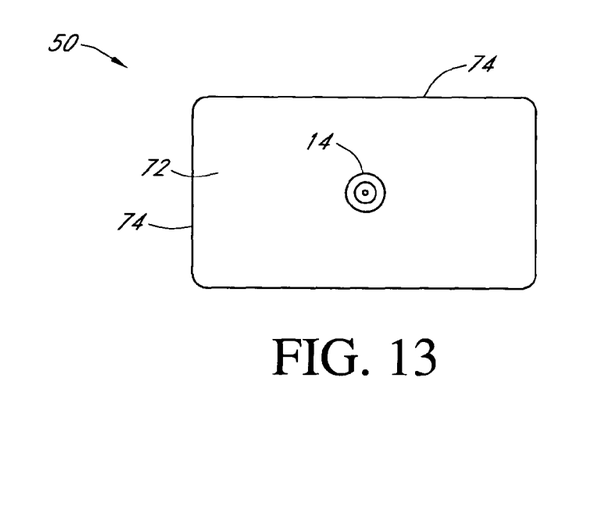
FIG. 13 is a top view of an embodiment of a fluid delivery device having a rectangular outer shape.

Another embodiment of a fluid delivery device 70 is illustrated in FIG. 13. As shown, the fluid delivery device 70 comprises a rectangular envelope 72 having a valve 14. It is contemplated that the rectangular envelope 72 may comprise any number and/or combination of the sheets and interior chambers discussed herein. The sheets comprising the rectangular envelope 72 are attached to one another by a seal 74. Depending on the particular sheets comprising the rectangular envelope 72, operation of the fluid delivery device 70 is substantially similar to the operation of the devices 10, 30 or 40.

Figure 14:
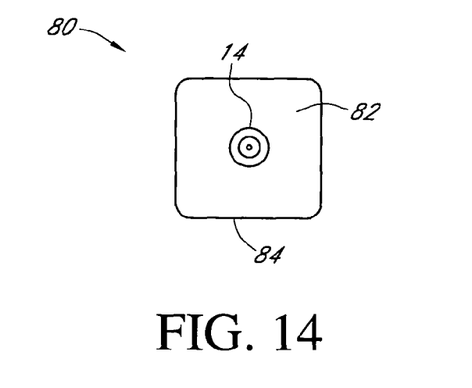
FIG. 14 is a top view of an embodiment of a fluid delivery device having a square outer shape.

It is contemplated that the dimensions of the rectangular envelope 72 may be changed so as to form other envelopes having different rectangular shapes and sizes, including but not limited to square-shaped envelopes. One embodiment of a fluid delivery device 80 having a square envelope 82 is shown in FIG. 14. As with the rectangular envelope 72 illustrated in FIG. 13, the square envelope 82 includes a one-way valve 14 positioned generally in the center of the envelope 72.

The square envelope 82 may comprise any number and/or combination of the sheets discussed herein. The sheets are sealed to one another by a peripheral seal 84. Depending on the particular sheets comprising the square envelope 82, operation of the fluid delivery device 80 is substantially similar to the operation of the device 10, 30 or 40.

Figure 15:
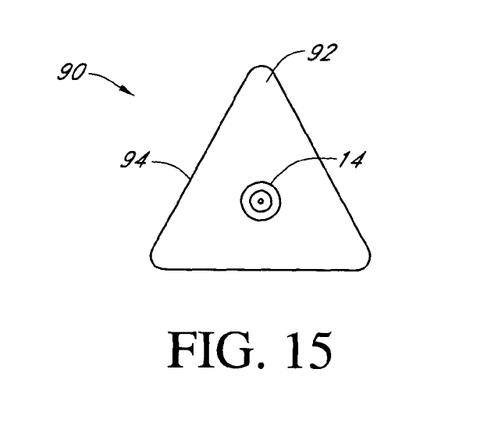
FIG. 15 is a top view of an embodiment of a fluid delivery device having a triangular outer shape.

FIG. 15 illustrates another embodiment of a fluid delivery device 90 comprising a triangular envelope 92. The triangular envelope 92 includes a valve 14, which is adapted to receive a luer connector. As with the devices discussed above, the triangular envelope 92 may comprise any number and/or combination of the sheets discussed herein. The sheets comprising the triangular envelope 92 are attached to one another by a peripheral seal 94. Depending on the particular sheets utilized within the triangular envelope 92, operation of the fluid delivery device 90 is substantially identical to the operation of the devices 10, 30 or 40.

Figure 16:
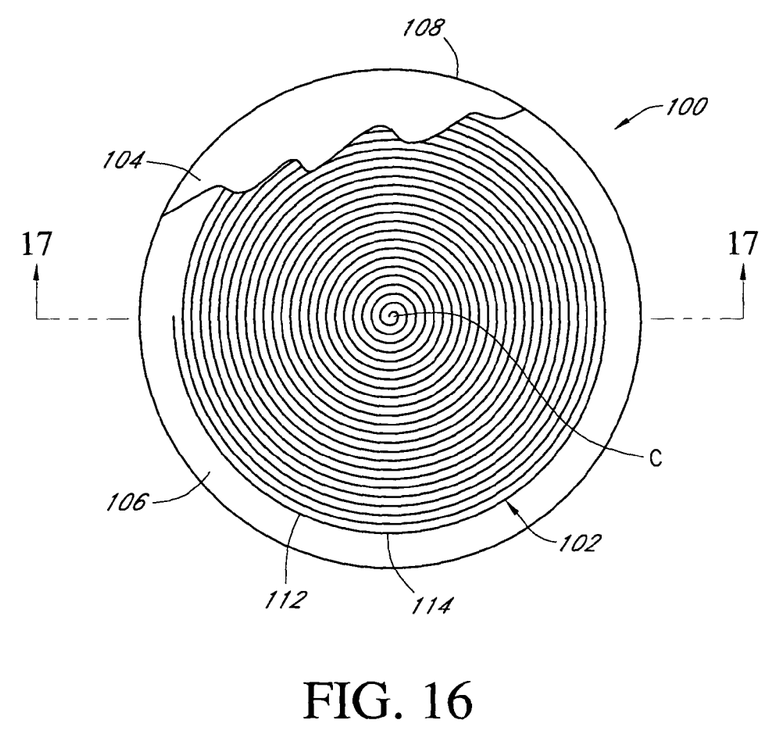
FIG. 16 is a top view of a fluid delivery device having a top layer partially cutaway to show a coiled wire diffusion layer of the device.
Figure 17:
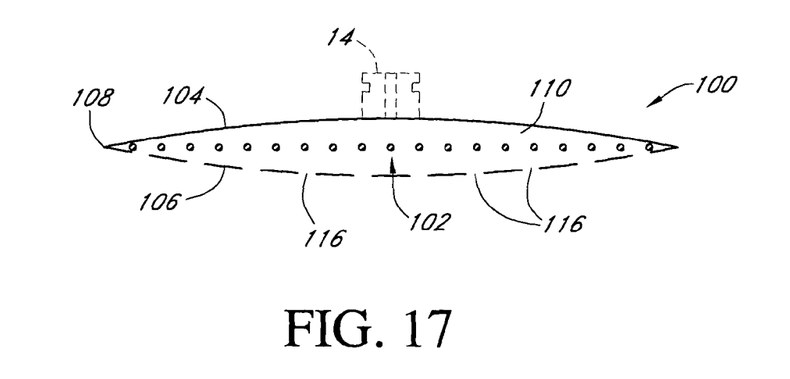
FIG. 17 is a side, cross-sectional view of the delivery device of FIG. 16, taken along line 17-17 of FIG. 16.

FIGS. 16 and 17 illustrate another embodiment of a fluid delivery device, generally referred to by the reference numeral 100. The fluid delivery device 100, preferably, is substantially similar to the device 30 of FIGS. 7 and 8, with the exception that the diffusion sheet 20 (of the device 30) is replaced by a coiled wire member 102. Desirably, in operation, the coiled wire member 102 permits fluid to pass through the member 102 at a controlled rate and in a substantially uniform manner over the area of the coiled wire member 102.

As in the previous embodiments, the fluid delivery device 100, includes an upper layer 104 and a lower layer 106. Preferably, the upper and lower layers 104, 106 are joined by a peripheral seal 108. The coiled wire member 102 is positioned within the space, or fluid reservoir 110, between the upper layer 104 and the lower layer 106. The coiled wire member 102 may vary in overall size, but preferably covers a significant portion of the lower layer 106. More preferably, the coiled wire member 102 covers substantially all of the lower layer 106 such that a substantial portion of the fluid within the reservoir 110, and preferably substantially all of the fluid within the reservoir 110, passes through the coiled wire member 102 before exiting the device 100.

In the illustrated arrangement, the coiled wire member 102 is constructed from a singular wire element 112 manipulated to expand from a center point C, in a substantially constantly increasing radius, into a coiled shape. Accordingly, a substantially constant gap 114 is defined between adjacent portions of the wire 112. Such an arrangement facilitates the controlled rate and uniform diffusion function of the member 102. In other arrangements, however, the coiled wire member 102 may be constructed from a plurality of individual rings, incrementally increasing in diameter and secured to one another. Other arrangements may utilize a singular wire element formed into shapes other than circular, but preferably defining a substantially constant gap between adjacent portions of the wire. Furthermore, the wire element 112 may assume a variety of cross-sectional shapes including, but not limited to, circular or rectangular. In one arrangement, the wire element 112 may be formed such that the adjacent coils are in contact along at least a portion of the coiled wire member 102. In such an arrangement, fluid may pass through small gaps in the adjacent coils or as a result of the coiled wire member 102 stretching in response to fluid pressure.

Preferably, as illustrated in FIG. 17, the coiled wire member 102 is substantially planar so as to facilitate adhesion to one or both of the layers 104, 106, if desired. In a preferred arrangement, at least a portion of the coiled wire member 102 is secured to the lower layer 106. The coiled wire member 102 may be secured to the lower layer 106 along the entire length of the lower surface of the wire element 112. Alternatively, the member 102 may be secured to the lower layer 106 at one or more distinct points or regions of the wire element 112, such as along an outer circumference of the member 102 or central portion of the member 102, for example. Advantageously, with such an arrangement, the coiled wire member 102 may be capable of expansion and retraction to alter the size of the gap 114 between adjacent portions of the wire element 112 in response to pressure exerted by fluid within the device 100.

Any suitable method may be used to secured the coiled wire member 102 to one or more of the layers 104, 106 including, but not limited to, chemical or thermal bonding. In the illustrated embodiment, the coiled wire member 102 covers only a portion of the lower layer 106 of the fluid delivery device 100. However, in an alternative embodiment, the coiled wire member 102 may cover substantially the entire lower layer 106 and, optionally, may be secured within the peripheral seal 108 between the upper and lower layers 104, 106.

Preferably, the lower layer 106 includes a plurality of openings 116 to permit fluid to pass out of the fluid reservoir 110. Collectively, the openings 116 define a fluid diffusion area of the delivery device 100. Desirably, the openings 116 cover a substantially equivalent, although slightly smaller, area of the lower layer 106 than an area covered by the coiled wire member 102. Therefore, fluid within the fluid reservoir 110 passes through the gaps 114 of the coiled wire member 102 before passing through the openings 116, and exiting the device 100.

Preferably, similar to the embodiments described above, the fluid delivery device 100 employs an adhesive in the form of an adhesive layer on an external surface of the lower layer 106 to permit the device 100 to be securably positioned on the skin of a patient. The adhesive may cover the entire external surface of the lower layer 106, or only a portion thereof. In one arrangement, the adhesive is provided only on a periphery of the external surface of the lower layer 106. A wrap or bandage may also be used, alone or in complement with an adhesive, to secure the device 100 in a desired position on the skin of a patient. In addition, the fluid delivery device 100 is provided with a fluid inlet 14 to permit fluid to be introduced into the fluid reservoir 110 and, desirably, to permit connection of the device 100 to an external source of fluid, as described in relation to the embodiments above.

Figure 18:
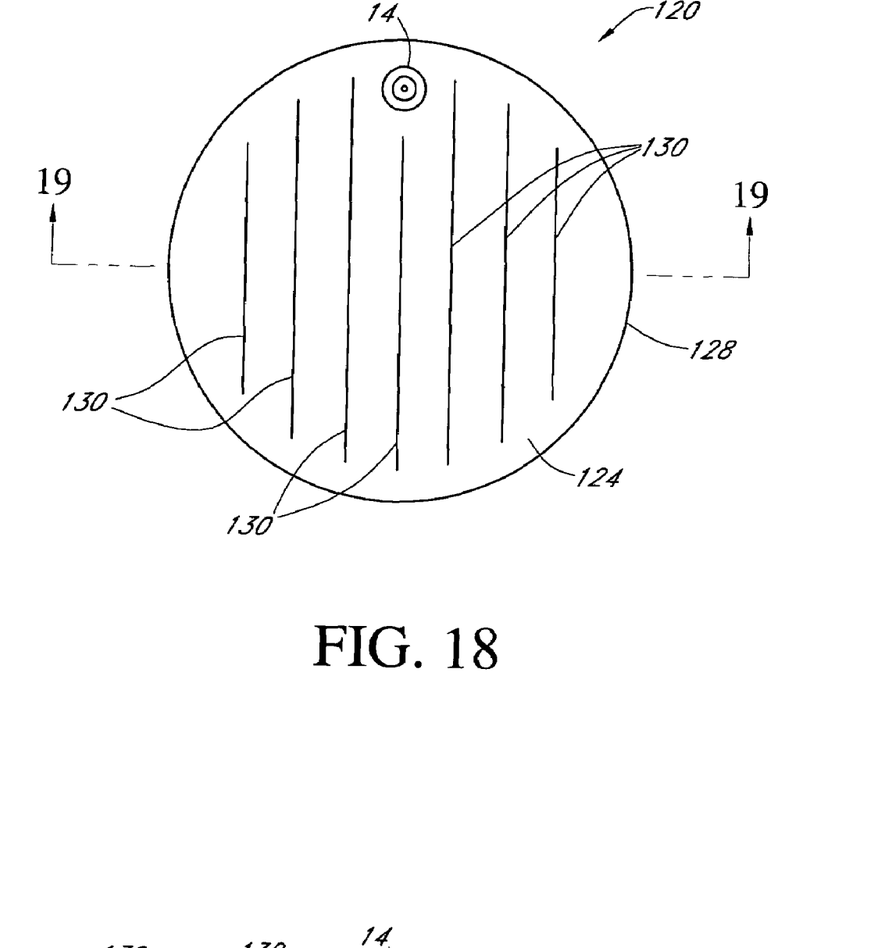
FIG. 18 is a top view of a fluid delivery device having a plurality of linear seams dividing the interior reservoir into a plurality of interconnected regions, or flow channels.
Figure 19:
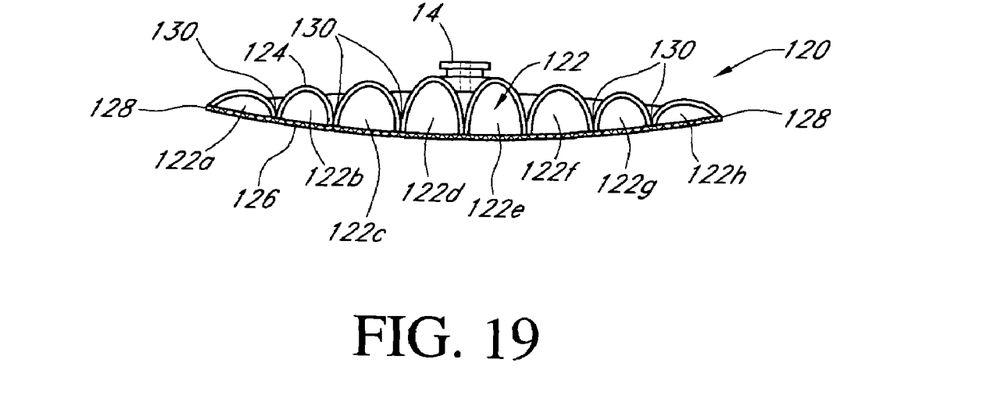
FIG. 19 is a side, cross-sectional view of the delivery device of FIG. 18, taken along the line 19-19.

With reference to FIGS. 18 and 19, another embodiment of a fluid delivery device, referred to generally by the reference numeral 120, is illustrated. The fluid delivery device 120 is similar to the above-described embodiments in that the device 120 defines a fluid reservoir 122 between an upper layer 124 and a lower layer 126 joined by a peripheral seal 128. Preferably, the upper layer 124 comprises a fluid impermeable sheet and the lower layer 126 comprises a fluid semi-permeable sheet. Desirably, the fluid semi-permeable sheet is configured to permit fluid to pass therethrough at a controlled, substantially uniform rate. However, the device 120 may alternatively be constructed from more than two layers, as described above in relation to the device 30 of FIGS. 7 and 8, the device 40 of FIGS. 9 and 10, and the device 100 of FIGS. 16 and 17. In addition, the delivery device 120 preferably includes an inlet 14 to permit fluid to be introduced into the reservoir 122 and to permit the device 120 to be connected to an external fluid source.

The fluid delivery device 120 differs from the above-described embodiments primarily in that the fluid reservoir 122 of the device 120 is segmented into a plurality of interconnected regions 122a-h. In the illustrated embodiment, the regions 122a-h are defined by a plurality of seams 130 created by securing the upper layer 124 to the lower layer 126, preferably along a linear or curvilinear path. For efficiency in the manufacturing process, it is preferred to form the seams 130 simultaneously with the formation of the peripheral seal 128. However, the seams 130 and peripheral seal 128 may also be created in separate process steps. In addition, other suitable methods of defining individual regions within the reservoir 122 may also be used.

Collectively, the regions 122a-h define a plurality of "flow channels" within the interior chamber, or reservoir 122. It is contemplated that the flow channels are sized and positioned within the device 120 so as to provide a substantially uniform distribution of the fluid to the lower, semi-permeable layer 126. Desirably, the flow channels divide the fluid within the device 120 such that the pressure exerted on the fluid, by the device 120 itself or an external source of pressure, is more evenly distributed to the fluid. As a result, the diffusion of fluid is more uniform over the diffusion area defined by the device 120. Moreover, it is contemplated that the size and/or shape of the flow channels is further influenced by the particular type of fluid which is intended to be diffused through the fluid delivery device 120, and/or the overall shape of the device 120. For example, in the device 120 of FIGS. 18 and 19, the device 120 is of a circular shape and the seams 130 are linear, and arranged substantially parallel to one another.

Figure 20:
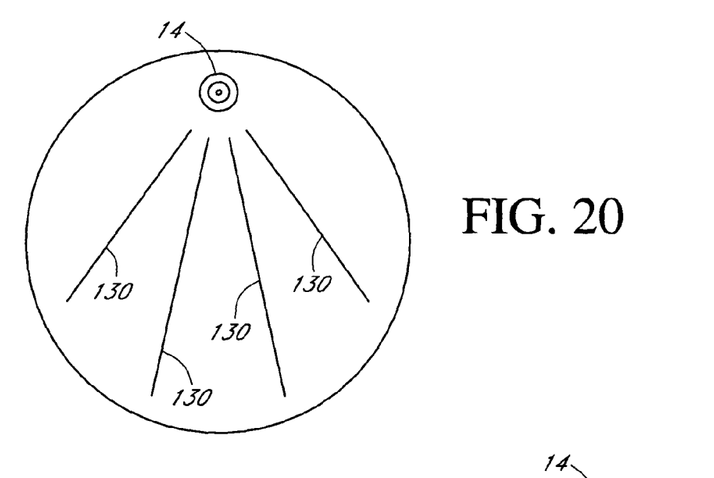
FIG. 20 is a top view of a modification of the fluid delivery device of FIG. 18, wherein the seams radiate outwardly from a fluid inlet positioned proximate an edge of the device.
Figure 21:
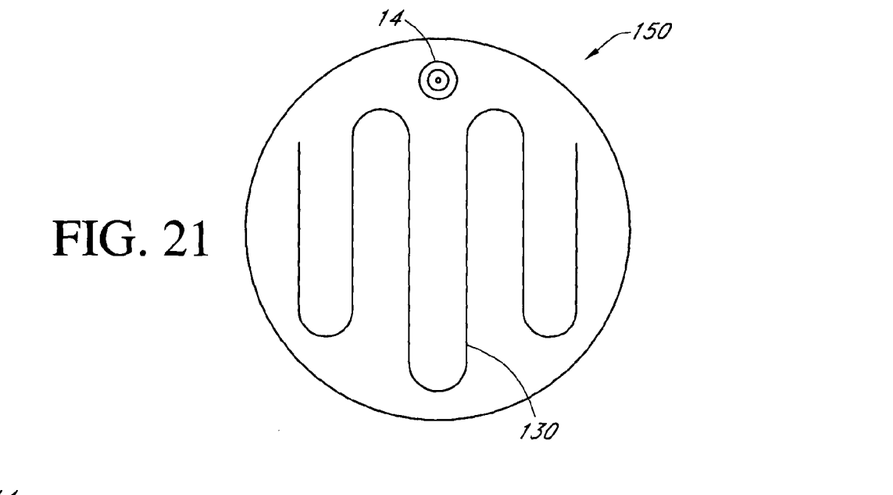
FIG. 21 is a top view of another modification of the fluid delivery device of FIG. 18, wherein a single seam includes a series of linear portions serially connected with one another to divide the internal reservoir into essentially two portions.
Figure 22:
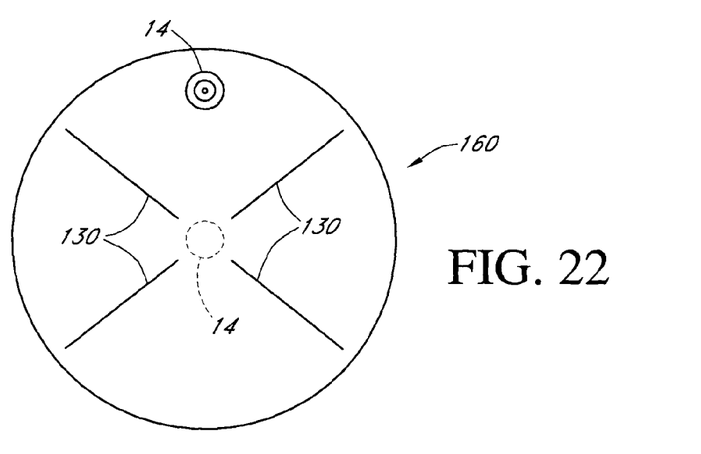
FIG. 22 is a top view of yet another modification of the fluid delivery device of FIG. 18, wherein a plurality of seams radiate outwardly from a center point of the device. A fluid inlet may be located proximate an edge of the device, as shown in solid line, or it may be located approximately in the center of the device, as shown in phantom.

FIGS. 20-22 illustrate additional fluid delivery devices, 140, 150 and 160, which are substantially similar to the device 120 of FIGS. 18 and 19. In the circular device 140 of FIG. 20, a fluid inlet 14 is positioned near an edge of the device 140 and the seams 130 radiate outwardly from approximately a center point of the inlet. Thus, fluid introduced into the device 140 is separated into the flow channels created by the plurality of seams 130, wherein the pressure exerted onto the fluid by the device 120, or an external pressure source, is more evenly distributed to the fluid and results in a more uniform delivery of the fluid.

FIG. 21 illustrates a circular fluid delivery device 150 having a single seam 130 formed into a meandering shape to define a plurality of substantially parallel sections of the seam 130, which are connected to one another in series. A fluid inlet 14 is positioned adjacent an edge of the device 150.

FIG. 22 illustrates a circular fluid delivery device 160 wherein a plurality of seams 130 radiate outwardly from approximately a center point of the device 160. The fluid inlet 14 may be positioned adjacent an edge of the device 160, as shown in solid line, or alternatively may be centrally positioned, as shown in phantom.

Although preferred embodiments of the invention have been described in detail, certain variations and modifications will be apparent to those skilled in the art, including embodiments that do not necessarily provide all of the features and benefits described herein. That is, some embodiments may exemplify one or more features or benefits, while other embodiments exemplify other features or benefits. Accordingly, the scope of the invention is not to be limited by the illustrations or the foregoing descriptions thereof, but by the claims that follow.

What is claimed is:

1. A fluid medication delivery device, comprising:
   a fluid impermeable layer;
   a fluid semi-permeable layer, said semi-permeable layer and said impermeable layer cooperating to define a space therebetween, said space defining a fluid reservoir of said delivery device, said semi-permeable layer and said impermeable layer having a continuous seal therebetween to define a periphery of said fluid reservoir;
   at least one internal wall within the periphery of said fluid reservoir configured so as to form multiple interconnected regions within said fluid reservoir, each said internal wall formed by securing a portion of said fluid impermeable layer located inside said periphery to a portion of said fluid semi-permeable layer located inside said periphery such that said portion of said fluid impermeable layer abuts said portion of said fluid semi-permeable layer; and
   a fluid inlet communicating with said fluid reservoir, said fluid inlet comprising a valve configured to permit fluid entry into said fluid reservoir, said fluid inlet adapted to permit said delivery device to be selectively connectable to a connector for a supply of fluid, said delivery device adapted to selectively secure said connector in the radial and axial direction, wherein said valve comprises a one-way valve configured such that, when said connector is secured to said fluid inlet, said one-way valve permits fluid to enter said fluid reservoir and prevents fluid from exiting said fluid reservoir through said fluid inlet;
   wherein a fluid is diffusable across said semi-permeable layer in response to a pressure imparted on said fluid.

2. The delivery device of claim 1, wherein said semi-permeable layer comprises a porous membrane having a pore size of less than 0.25 microns.

3. The delivery device of claim 1, wherein said at least one internal wall is defined by a seal between said impermeable layer and said semi-permeable layer.

4. The delivery device of claim 1, wherein said semi-permeable layer comprises a material selected from one of polysulfone, polyethersulfone, polyvinylidene diflouride, and nylon.

5. The delivery device of claim 1, wherein said connector is a luer coupler.

6. The delivery device of claim 1, wherein said fluid inlet is configured to remain connected to said supply of fluid.

7. The delivery device of claim 1, wherein said fluid inlet is configured to allow the continuous delivery of fluid to the fluid medication delivery device from said supply of fluid.

8. A fluid medication delivery device, comprising:
   a fluid impermeable layer;
   a fluid semi-permeable layer configured such that a fluid is diffusable across said semi-permeable layer, said semi-permeable layer and said impermeable layer cooperating to define a space therebetween, said space defining a fluid reservoir of said delivery device, said semi-permeable layer and said impermeable layer having a continuous seal therebetween to define a periphery of said fluid reservoir;
   at least one seam inside the periphery of said fluid reservoir that is configured to segment said fluid reservoir into multiple interconnected regions, said seam formed by securing a portion of said fluid impermeable layer located inside the periphery to a portion of said fluid semi-permeable layer located inside the periphery such that said portion of said fluid impermeable layer abuts said portion of said fluid semi-permeable layer; and
   a fluid inlet communicating with said fluid reservoir, said fluid inlet comprising a valve configured such that, when said connector is secured to said fluid inlet, said valve permits fluid entry into said fluid reservoir, said fluid inlet adapted to permit said delivery device to be selectively connectable to a connector for a supply of fluid.

9. The fluid medication delivery device of claim 8, wherein a portion of said at least one seam is linear.

10. The fluid medication delivery device of claim 8, wherein a portion of said at least one seam is curvilinear.

11. The fluid medication delivery device of claim 8, comprising a plurality of linear seam portions that radiate outwardly from said fluid inlet.

* * * * *